United States Patent

Peterson et al.

[11] Patent Number: 5,808,301
[45] Date of Patent: Sep. 15, 1998

[54] TESTING OF PROPERTIES IN FLOWABLE MATERIALS

[75] Inventors: John P. Peterson, Chapel Hill; Paul Brinkley, Morrisville, both of N.C.

[73] Assignee: Northern Telecom Limited, Montreal, Canada

[21] Appl. No.: 769,131

[22] Filed: Dec. 18, 1996

[51] Int. Cl.[6] .......................... G01N 21/25; G01N 21/35
[52] U.S. Cl. ...................... 250/343; 250/339.12
[58] Field of Search ................... 250/339.12, 339.08, 250/343

[56] References Cited

U.S. PATENT DOCUMENTS

| | | | |
|---|---|---|---|
| 4,227,083 | 10/1980 | Sherinski | 250/343 |
| 4,649,711 | 3/1987 | Sibley et al. | 250/343 X |
| 4,717,827 | 1/1988 | Harvey | 250/343 |
| 4,888,484 | 12/1989 | Harvey | 250/343 |

*Primary Examiner*—Edward J. Glick
*Attorney, Agent, or Firm*—Foley & Lardner

[57] ABSTRACT

Method of testing a property of a flowable substance. In particular this invention relates to the testing of the cross-linkability of an adhesive and is particularly relevant to an in-line process for mounting electronic components upon a printed circuit board. In the process, infrared light is passed through adhesive being fed to a dispensing position. Some of the light is absorbed by chemicals in the adhesive. Unabsorbed light after passing through the adhesive is analyzed and wavelengths of the light relating to cross-linkable materials in adhesive are monitored.

7 Claims, 3 Drawing Sheets

TESTING OF PROPERTIES IN FLOWABLE MATERIALS

BACKGROUND OF THE INVENTION a) Field of the Invention

This invention relates to the testing of properties in flowable materials.

b) Relevant Prior Art

In the use of certain flowable materials in manufacturing industries, it is sometimes paramount that these materials maintain certain properties for ensuring that the manufacturing processes are performed in a satisfactory manner and without endangering the final product, i.e. without reducing quality or resulting in product failure. For instance, in the manufacture of printed circuit board assemblies, surface mount components are affixed to board circuitry by either of two processes, i.e. reflow soldering and wave soldering. In a reflow soldering process, solder paste is applied to terminal positions of the board circuitry on a surface of the board and the surface mount components are positioned accurately in their required locations on the board with the terminals of the components directly above the terminal positions of the board circuitry. Finally, the board is heated to activate the solder thereby joining the component terminals to the terminals on the board. In contrast, in the wave soldering process, the electronic components are mounted in position on a printed circuit board preparatory to soldering the components and are held in these positions by a curable adhesive. The adhesive is then cured to set the components in position before the soldering operation.

Unfortunately, the success or failure of making a successfully completed printed circuit board assembly depends to a large degree on the suitability of the adhesive actually being used. It has been found that even if excellent adhesive quality standards are maintained by an adhesive manufacturer, the adhesive properties may change subsequently to render the adhesive extremely suspect as to its usefulness for the particular purpose. Supplies of cross-linkable adhesive should be stored at low temperatures to slow any cross-linking activity and should be in dark storage to prevent light encouraged cross-linking. However, on a practical basis, supplies of adhesive are stored for different time periods and under different temperatures before use and the adhesive properties thereby differ from adhesive unit to adhesive unit and different degrees of cross-linking exist in the adhesive units at commencement of use. Should cross-linking of an adhesive have proceeded to a certain degree before use, it is found that its adhesive property is extremely suspect and the adhesive may not be capable of holding at least some electronic components in position prior to a wave soldering operation. As a result, in the finished board assembly, there are missing electronic components. This leads either to high cost and volume of scrapboard assemblies or the cost and labour involved in locating and replacing the missing components is extremely high.

Even when an adhesive unit is mounted in position for use, it is accessible to light and to ambient temperatures which tend to increase the rate of cross-linking. It follows that sometimes an adhesive unit having desired adhesive properties will progressively cross-link as use continues. It is impractical on a commercial basis to chemically test valid samples of adhesive units before the units are placed in use. Even if such an exercise were to be instituted, apart from the expense, labour and inconvenience involved, no guarantee of continued usefulness of any particular unit could be given. On a slow production run wherein stoppage in production occurs, an adhesive unit may cross-link to a degree that its adhesive properties become suspect. Such a situation may arise after only a few days of use. Until problems are discovered with missing components on boards, the deterioration in adhesive quality is unknown. This deterioration cannot be judged by the flowability of the adhesive which is still capable of being fed or pumped in required fashion to locations for connecting electronic components to printed circuit boards.

SUMMARY OF THE INVENTION

The present invention seeks to provide a method of testing properties of a flowable material which may be used for testing the properties of flowable adhesive used for attaching electronic components to a printed circuit board and which will assist in minimizing or avoiding the above problems.

Accordingly, the present invention provides a method of testing the quality of a particular property of a flowable substance comprising passing infrared light having a range of wavelengths through the substance to cause different wavelengths of the infrared light to be absorbed at least partially by different materials in the substance; receiving the unabsorbed infrared light which has passed through the substance; and generating signals corresponding to the different wavelengths of the unabsorbed infrared light to enable a determination to be made of the quality of the particular property of the substance.

In the use of the method defined above, in practice, it is convenient to apply the test with the substance flowing past a test position. In this way, any change in quality of the property of the substance may be noted and monitored.

More particularly, and according to a further aspect of the present invention, there is provided a method of testing the cross-linkability of a cross-linkable flowable adhesive comprising: passing infrared light having a range of wavelengths through the adhesive to cause different wavelengths of the infrared light to be absorbed at least partly by different materials in the adhesive; receiving the unabsorbed infrared light which has passed through the adhesive; and generating signals corresponding to the different wavelengths of the unabsorbed infrared light to enable a determination to be made of the amount of non-cross-linked and cross-linkable material existing in the adhesive.

In the above method for testing for the cross-linkable property of the adhesive, it is of particular and practical use to test the cross-linkability either continuously or intermittently so that monitoring of the property is performed. This is of particular interest when the adhesive is being passed through a feed line as infrared light may be passed through the feed line either continuously or intermittently.

The invention further includes apparatus for testing the cross-linkability of an adhesive in use in an on-line production assembly for a product comprising: an adhesive dispensing station in the line; means for passing infrared light through adhesive to be disposed in the dispensing station; means for receiving infrared light which is unabsorbed by materials in the adhesive and which has passed through the adhesive, the infrared light having an operating range of wavelengths; and means for generating signals corresponding to the different wavelengths of unabsorbed infrared light to enable a determination to be made of the amount of non-cross-linked and cross-linkable material existing in the adhesive.

BRIEF DESCRIPTION OF THE DRAWINGS

One embodiment of the invention will now be described, by way of example, with reference to the accompanying drawings, in which.

DESCRIPTION OF A PREFERRED EMBODIMENT OF THE INVENTION

Figure 1:
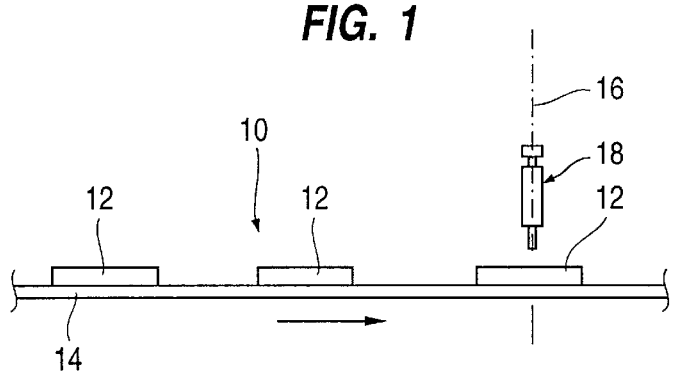
FIG. 1 is a diagrammatic side elevational view of part of an in-line assembly apparatus for assembling electronic components onto printed circuit: boards.

In the embodiment, apparatus 10 for soldering components onto printed circuit boards 12 comprises, in known manner, a conveyor 14 for transporting the printed circuit boards 12 intermittently in series through an adhesive dispensing station 16. At least one adhesive dispensing holder 18 is positioned in the station 16, one holder only being shown in FIG. 1. The or each holder is operable in normal fashion by raising and lowering the holder (by means not shown) towards and away from each printed circuit board 12 as the board is presented within the adhesive dispensing station for the holder to apply adhesive in appropriate positions for location of electronic components onto the board.

As shown in greater detail in FIG. 2, the or each holder 18 is provided with a dispensing line comprising a vertical rigid metal outlet tube 20 having a lower end 22 which engages the upper surface of a board in the station 16 while a given quantity of adhesive 24 is deposited upon a chosen board site for retaining an electronic component to be subsequently positioned upon the board.

The embodiment differs from the conventional apparatus described above in that, according to the invention, the embodiment also includes an apparatus for testing the cross-linkability of the adhesive in the holder 18.

Figure 3:
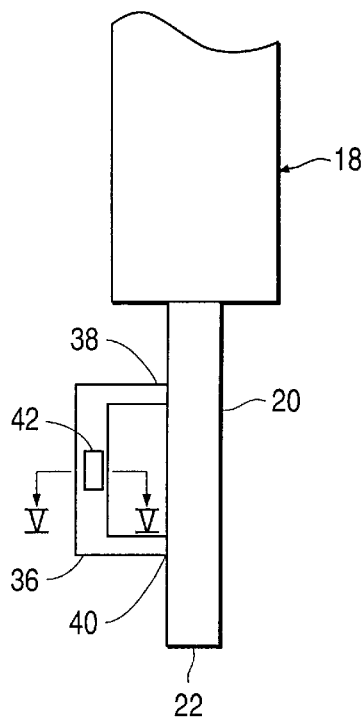
FIG. 3 is a side elevational view of part of the adhesive applicator of FIG. 2 and to a larger scale.
Figure 4:
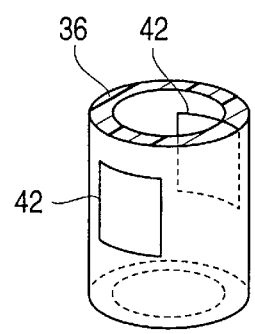
FIG. 4 is an isometric view of part of the applicator of FIG. 3 and to a yet larger scale.
Figure 2:
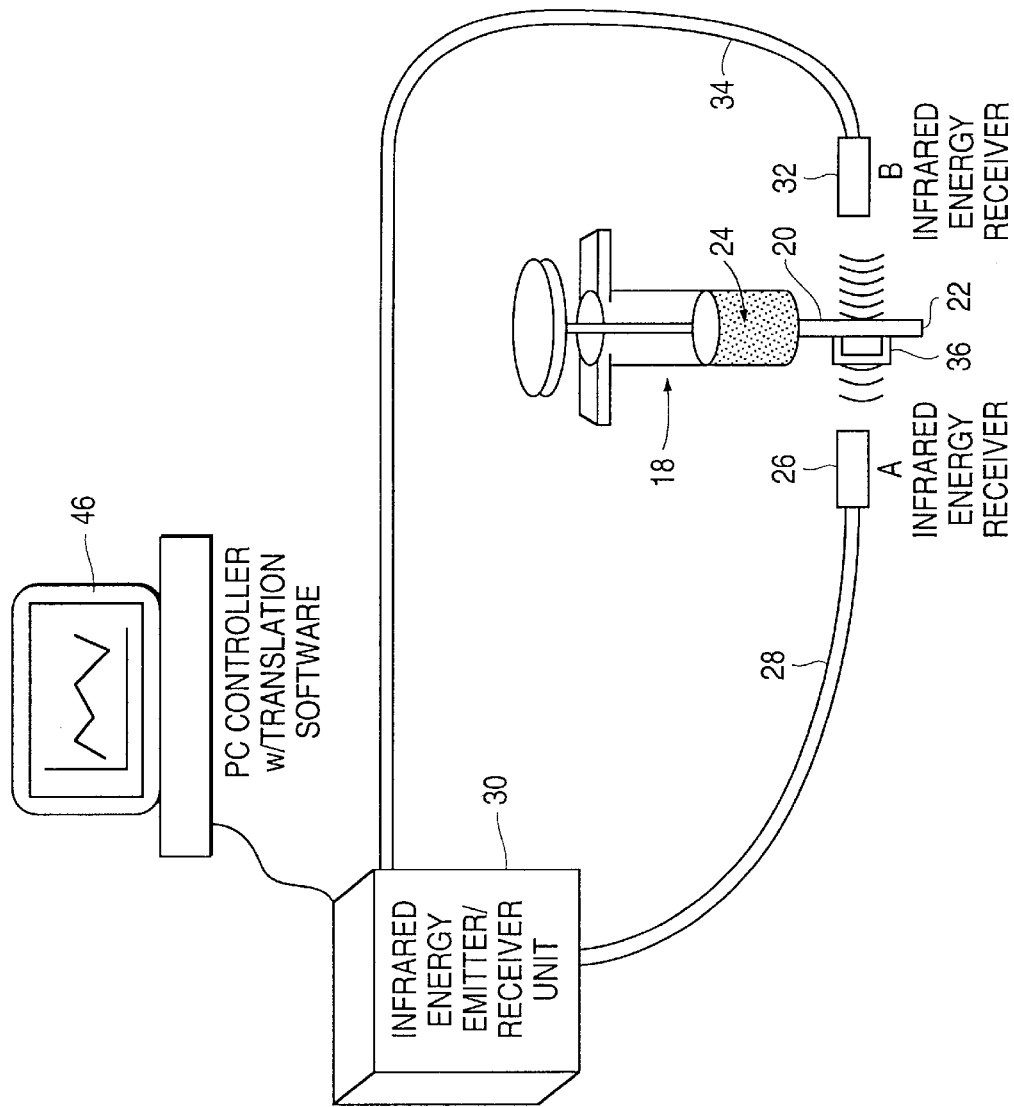
FIG. 2 is a diagrammatic view of apparatus for testing the cross-linkability of adhesive to be applied to a printed circuit board and to a much larger scale than FIG. 1.

As shown in FIGS. 2, 3 and 4, the embodiment also includes, as part of the test apparatus, means for directing infrared light through the adhesive and means for receiving infrared light which has not been absorbed by the adhesive and the part of the holder through which light has been directed. The means for directing the light through the adhesive comprises an infrared light transmitting lens 26 which is a focusing lens. The lens 26 is provided with a supply optical cable 28 extending from a source of infrared light which is a Fourier transform-infrared analyzer 30 (referred to herein as "ft-ir"). The means for receiving the unabsorbed infrared light comprises an infrared light receiving lens 32 having a return optical cable 34 to the ft-ir 30.

Figure 5:
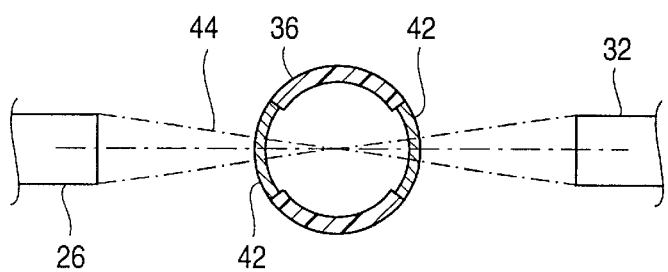
FIG. 5 is a cross-sectional view through the adhesive applicator taken along line V—V in FIG. 3.

In the test apparatus, the outlet: tube 20 provides a primary line of the dispensing line and a secondary or loop line 36 is also provided (see particularly FIGS. 3 to 5). This secondary line extends outwardly from the outlet tube 20 and is interconnected with the outlet tube 20 at spaced upper and lower positions by an inlet 38 and an outlet 40 of the line 36. As the tube 20 will absorb substantial amounts of infrared light and make any test using infrared light extremely difficult if not impossible, the line 36 is provided to enable light to pass into and out from the adhesive contained at any moment within the line 36 while being substantially unabsorbed except for the absorption caused by the adhesive itself. For this purpose, the line 36 is conveniently formed from a plastic tube which is suitable for passage of the adhesive and into the tube are provided two diametrically opposed rectangular regions 42, these regions being of infrared light transmitting and substantially non-absorbing material. Various materials are known with these required properties and these materials include potassium bromide or sodium chloride prepared in a particular known fashion for providing windows having the requirements for each of the regions 42.

As shown in FIGS. 4 and 5, the two lenses 26 and 32 are positioned one on each side of the tube 36 so as to transmit light from the lens 26 through the two regions 42 to be received by the lens 32 on the other'side of the tube. The lens 26 is positioned such that the focused light 44 (FIG. 5) has its focal point within the adhesive in the tube 36. Differences in wavelengths of the infrared light transmitted and received by the ft-ir 30 are shown upon a visual monitor 46 for instance as shown diagrammatically in FIG. 2.

In use of the apparatus of the embodiment, printed circuit boards are moved intermittently by the conveyor 14 through the adhesive application station 16 to have adhesive applied by the holder 18 in the desired locations for positioning surface mount components upon the boards. During the use of the adhesive and the operation of the in-line apparatus, infrared light is passed through the regions 42 of the line 36 either on an intermittent or a continuous basis so that an intermittent or continuous comparison may be made by the ft-ir 36 between the infrared light transmitted and received by the ft-ir. The difference in the wavelengths of the infrared light transmitted and received and as noted by the ft-ir represent the absorption units of the wavelengths of infrared light and thereby represent the chemistry of the materials actually existing at that particular time. In particular, the absorption characteristics of the infrared light represent the amount of cross-linkable material still existing in the adhesive. Thus in practice, the infrared light passing from lens 26 to 32 is absorbed at its different wavelengths by the different chemicals within the adhesive and which partially absorb the infrared light at those wavelenths and this information is fed by the outlet optical cable 34 back to the ft-ir 30.

Figure 6:
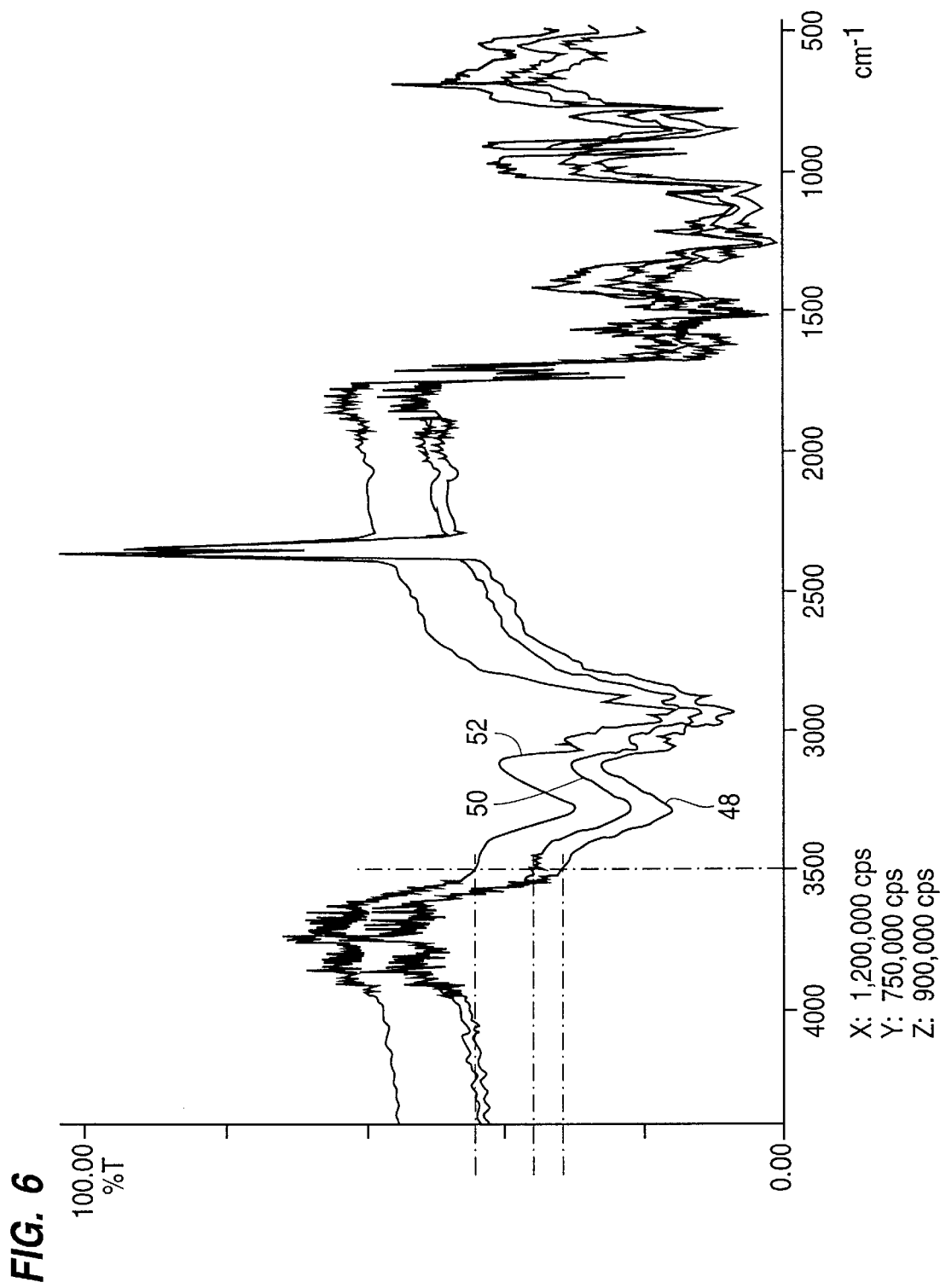
FIG. 6 is a representation of a visual readout of concentration of materials in the adhesive in the applicator at different stages of the operation.

This information is then shown graphically upon the visual monitor 46, for instance, by the manner shown by the graphs represented upon FIG. 6. In FIG. 6, the vertical axis relates to the absorption units of the wavelengths of infrared light between 0 and 100% and the horizontal axis represents the actual wavelengths of the light which is being transmitted. As shown in the graphs, the wavelengths in the region around 3500 Hz represent the chemicals within the adhesive which are concerned with cross-linkability. Cross-linking proceeds upon the release of hydrogen atoms from oxygen atoms on a progressive basis, the hydrogen atoms being progressively replaced by carbon atoms to give an oxygen-carbon bond. This process is indicated by a change in the graph in the region around 3500 Hz as indicated above. The lower graph 48 in FIG. 6 is produced by an adhesive which has a viscosity of about 750,000 cps and is found to be eminently suitable for use in mounting electronic components onto printed circuit boards. In this adhesive the cross-linkability is shown by relatively low absorption unit percentage in the vertical axis at around 3500 Hz. However, as cross-linking progresses for adhesive passing through the tube 36, the absorption units increase at around 3500 Hz. Thus, it is found at about 900,000 cps (graph 50), a higher absorption unit percentage is obtained as oxygen-carbon bonding proceeds. This is still acceptable for purposes of mounting components onto a printed circuit board. However, as cross-linking of the adhesive increases further, a graph similar to graph 52 is obtained. This is at a viscosity level of about 1,200,000 cps in which the absorption unit percentage level is so high at around 3500 Hz, that the degree of cross-linking which has already occurred within the adhesive makes it unreliable for its intended component mounting purpose. At this graph position the adhesive should be discarded and replaced. Hence, with the use of this testing equipment, upon the profile of the graph represented upon the visual display being such as to place the cross-linkability in any doubt, then this adhesive may be immediately withdrawn and replaced.

The apparatus also of course will test for the remaining cross-linkability of a new unit of adhesive immediately it is placed within the adhesive application station so that the complete unit may be immediately discarded and replaced with more suitable material.

As may be seen from the above embodiment, with the use of the test apparatus, the cross-linkable quality remaining in an adhesive may be carefully monitored with the result that it is ensured that any electronic components which are placed upon the board to be held by this particular adhesive must remain upon the board during the completion of the wave soldering operation.

What is claimed is:

1. A method of testing the quality of a particular property of a flowable substance comprising:

passing infrared light having a range of wavelengths through the substance to cause different wavelengths of the infrared light to be absorbed at least partially by different materials in the substance, the passing step being accomplished by passing the infrared light into the substance as a beam of infrared light focused to a focal point within the substance, and by passing unabsorbed infrared light out of the substance from the focal point as a diverging beam of unabsorbed infrared light, the diverging beam of unabsorbed infrared light emerging both from the substance and from any container holding the substance;

receiving the unabsorbed infrared light which has passed though the substance and through any container holding the substance; and generating signals corresponding to different wavelengths of unabsorbed infrared light to enable a determination to be made of the quality of the particular property of the substance.

2. A method according to claim 1 comprising passing the infrared light through the substance as the substance is flowing passed a test position.

3. A method according to claim 1 comprising passing the substance through a feedline to a dispensing outlet and passing the infrared light through the feedline and through the substance as it is passing through the feedline, and generating signals corresponding to the different wavelengths of the infrared light unabsorbed by the substance in the feedline and by the feedline.

4. A method according to claim 3 comprising passing the infrared light continuously through the feedline and through the substance in the feedline over a period of time and generating signals successively and which correspond to the different wavelengths of unabsorbed infrared light passing through the feedline.

5. Apparatus for testing the cross-linkability of an adhesive in an on-line production assembly for a product comprising:

a production assembly line for the product;

an adhesive dispensing station in the production assembly line;

means for passing infrared light through adhesive to be disposed in the dispensing station, the means for passing the infrared light comprising a transmitting focusing lens to focus a beam of infrared light to a focal point within the adhesive;

means for receiving infrared light which is unabsorbed by materials in the adhesive and which has passed through the adhesive, the infrared light having an operating range of wavelengths, the means for receiving unabsorbed infrared light comprising a receiving lens provided to receive unabsorbed infrared light in the form of a divergent beam from the focal point; and means for generating signals corresponding to different wavelengths of unabsorbed light to enable a determination to be made of the amount of non-cross-linked and cross-linkable material existing in the adhesive.

6. Apparatus according to claim 5 having an adhesive dispensing holder containing adhesive in the dispensing station, the adhesive holder including a dispensing line and a storage facility and the means for passing the infrared light through the adhesive being positioned to pass the infrared light through the dispensing line.

7. Apparatus according to claim 6 wherein the dispensing line comprises a primary line and a secondary line which has an inlet and an outlet spaced apart in the secondary line and connecting it to the primary line, and the means for passing the infrared light is located to pass the infrared light through the secondary line.

* * * * *